United States Patent [19]

Karrer et al.

[11] 3,988,477

[45] Oct. 26, 1976

[54] ETHERS AND INSECTICIDAL COMPOSITIONS THEREWITH

[75] Inventors: Friedrich Karrer, Basel; Saleem Farooq, Aesch, both of Switzerland

[73] Assignee: Ciba-Geigy Corporation, Ardsley, N.Y.

[22] Filed: Apr. 17, 1975

[21] Appl. No.: 569,039

[30] Foreign Application Priority Data

Apr. 18, 1974 Switzerland............ 5362/74
Mar. 7, 1975 Switzerland............ 2907/75

[52] U.S. Cl. .......... 424/337; 260/609 F;
260/465 K; 260/571; 260/465 E; 260/576;
260/465 F; 260/611 A; 260/465 G; 424/330;
424/340; 260/340.5; 260/607 H
[51] Int. Cl.² .......... A01N 9/12; C07C 149/32
[58] Field of Search ........... 260/609 F; 424/337

[56] References Cited
UNITED STATES PATENTS

| 3,384,670 | 5/1968 | Reifschneider | 260/609 F |
| 3,409,676 | 11/1968 | Wilson | 260/609 F |
| 3,489,804 | 1/1970 | O'Shea | 260/609 F |
| 3,647,752 | 3/1972 | Giesiking et al. | 260/609 F |

FOREIGN PATENTS OR APPLICATIONS 1,911,799  3/1969  Germany............ 260/609 F

*Primary Examiner*—Lewis Gotts
*Assistant Examiner*—D. R. Phillips
*Attorney, Agent, or Firm*—Harry Falber; Frederick H. Rabin

[57] ABSTRACT

New phenyl-aralkyl ethers, thioethers and amines, their manufacture and use for the control of insects are disclosed. The compounds correspond to the formula

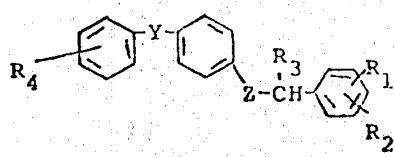

wherein
Y represents —S—, CH$_2$S— or

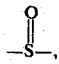

Z represents —S—, —O— or —NH—,
R$_1$ represents hydrogen, C$_1$–C$_4$-alkyl, C$_1$–C$_2$-alkoxy, C$_3$–C$_4$-alkenyloxy, C$_3$–C$_4$-alkynyloxy, C$_3$–C$_4$-haloalkenyloxy, halogen, CN or NO$_2$,
R$_2$ represents hydrogen, C$_1$–C$_4$-alkyl, C$_1$–C$_2$-alkoxy or halogen, or
R$_1$ and R$_2$ together represent the 3,4-methylenedioxy group, and
R$_3$ represents hydrogen or methyl, and
R$_4$ represents hydrogen, methyl or halogen.

17 Claims, No Drawings

ETHERS AND INSECTICIDAL COMPOSITIONS THEREWITH

The present invention relates to phenyl-aralkyl ethers, phenyl-aralkyl thioethers and phenyl-aralkyl amines, to processes for their production and to their use in pest control.

The phenyl-aralkyl ethers, phenyl-aralkyl thioethers and phenyl-aralkyl amines have the formula $$R_4 - \text{C}_6\text{H}_4 - Y - \text{C}_6\text{H}_4 - Z - \overset{R_3}{\underset{|}{C}}H - \text{C}_6\text{H}_3(R_1)(R_2) \quad (I)$$

wherein

Y represents —S—, —CH$_2$S— or $$-\underset{\underset{O}{\|}}{S}-,$$

Z represents —S—, —O— or —NH—, $R_1$ represents hydrogen, $C_1$–$C_4$-alkyl, $C_1$–$C_2$-alkoxy, $C_3$–$C_4$-alkenyloxy, $C_3$–$C_4$-alkynyloxy, $C_3$–$C_4$-haloalkenyloxy, halogen, CN or NO$_2$, $R_2$ represents hydrogen, $C_1$–$C_4$-alkyl, $C_1$–$C_2$-alkoxy or halogen, or $R_1$ and $R_2$ together represent the 3,4-methylenedioxy group, and $R_3$ represents hydrogen or methyl, and $R_4$ represents hydrogen, methyl or halogen.

Halogen is fluorine, chlorine, bromine or iodine. The alkyl, alkoxy, alkenyloxy, haloalkenyloxy or alkynyloxy groups given under $R_1$ and $R_2$ are straight-chain or branched-chain. Examples of such groups are: methyl, ethyl, n-propyl, isopropyl, methylthio, methoxy, ethoxy, β-chloroallyloxy, α-chloroallyloxy, allyloxy or propargyloxy.

Compounds of formula I particularly preferred on account of their action are those wherein Y represents —S— or $$-\underset{\underset{O}{\|}}{S}-,$$

Z represents —S—, —O— or —NH—, $R_1$ represents hydrogen, $C_1$–$C_4$-alkyl, methoxy, propargyloxy or halogen, $R_2$ represents hydrogen, $R_1$ and $R_2$ together represent the 3,4-methylenedioxy group, and $R_3$ and $R_4$ represent hydrogen.

A good action is exhibited also by compounds of formula (I) wherein

Y represents —S—,

Z represents —O— or —S—, $R_1$ represents hydrogen, 4-ethyl, 4-i-propyl, 4-methyl, 4-propargyloxy, 4-sec.butyl, 4-methoxy or 4-bromine, $R_2$ represents hydrogen, or $R_1$ and $R_2$ together represent the 3,4-methylenedioxy group, and $R_3$ and $R_4$ represent hydrogen.

The compounds of formula I are produced by methods known per se, for example as follows:

1) $\underline{Z = -O- \text{ or } -S-,}$ $$R_4-\text{C}_6\text{H}_4-Y-\text{C}_6\text{H}_4-ZMe + X-\overset{R_3}{\underset{|}{C}}H-\text{C}_6\text{H}_3(R_1)(R_2) \xrightarrow{\text{base}} I$$

(II)   (III)

2) $\underline{Z= -NH-}$ $$R_4-\text{C}_6\text{H}_4-Y-\text{C}_6\text{H}_4-ZH + O=\overset{R_3}{\underset{|}{C}}-\text{C}_6\text{H}_3(R_1)(R_2) \xrightarrow{-H_2O}$$

(IV)   (V)

$$R_4-\text{C}_6\text{H}_4-Y-\text{C}_6\text{H}_4-Z=\overset{R_3}{\underset{|}{C}}-\text{C}_6\text{H}_3(R_1)(R_2) \xrightarrow[\text{catalyst}]{+H_2} I$$

(VI)

In the formulae II to VI, the symbols $R_1$ to $R_4$, Y and Z have the meanings given for formula I, and X stands for halogen, especially for chlorine or bromine, and Me for a metal of the 1st or 2nd main group of the periodic system, particularly for sodium, potassium or calcium.

The starting materials of formulae II, III, IV and V are known and can be produced by known methods.

Suitable acid-binding agents or bases are, e.g., tertiary amines such as trialkylamines, pyridine or dialkylanilines; also inorganic bases such as hydrides or hydroxides; alkoxides and carbonates of alkali metals and alkaline-earth metals. The processes 1 and 2 are performed at a reaction temperature of between —0° and 130° C, preferably at between 20° and 100° C, at normal pressure and in the presence of solvents or diluents. Suitable solvents or diluents are, e.g., ethers such as diethyl ether, diisopropyl ether, 1,2-dimethoxyethane, dioxane or tetrahydrofuran; N,N-dialkylated carboxylic acid amides such as dimethylformamide; aliphatic and aromatic hydrocarbons, especially benzene, toluene, xylenes or ethylbenzene or dimethylsulphoxide; ketones such as acetone, methyl ethyl ketone or cyclohexanone as well as hexamethylphosphoric acid amide.

Hydrogenation of compounds of formula VI to compounds of formula I is performed, e.g., with catalytically activated hydrogen, advantageously between room temperature and the boiling temperature of the reaction mixture and at normal or elevated pressure. Suitable catalysts are preferably Raney nickel, or noble metals such as platinum or palladium.

The compounds of formula I are suitable for the control of insects of the families: Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae.

The insecticidal action can be appreciable broadened and adapted to suit given circumstances by the addition of other insecticides and/or acaricides. Suitable additives are, e.g.:

organic phosphorus compounds,
nitrophenols and derivatives thereof,
formamidines, ureas,
carbamates,
chlorinated hydrocarbons, or
pyrethroids.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents that are inert to the active substances. The active substances can be obtained and used in the following forms:

solid preparations: dusts, scattering agents, granulates, coated granulates, impregnated granulates and homogeneous granulates;

liquid preparations:
 a. water-dispersible active-substance concentrates: wettable powders, pastes or emulsions,
 b. solutions.

The content of active substance in the described preparations is between 0.1 and 95%.

The active substances of formula I can be formulated, for example, as follows:

Dusts:
The following substances are used to prepare (a) a 5% dust, and (b) a 2% dust:
 a. 5 parts of active substance,
   95 parts of talcum;
 b. 2 parts of active substance,
   1 part of highly dispersed silicic acid,
   97 parts of talcum.

The active substances are mixed and ground with the carriers.

Granulate:
The following substances are used to produce a 5% granulate:
 5% parts of active substance,
 0.25 part of epichlorohydrin,
 0.25 part of cetyl polyglycol ether,
 3.50 parts of polyethylene glycol,
 91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder:
The following constituents are used in the preparation of (a) a 40%, (b) and (c) a 25%, and (d) a 10% wettable powder:
 a. 40 parts of active substance,
   5 parts of sodium lignin sulphonate,
   1 part of sodium dibutyl-naphthalene sulphonate,
   54 parts of silicic acid;
 b. 25 parts of active substance,
   4.5 parts of calcium lignin sulphonate,
   1.9 parts of Champagne chalk/hydroxyethyl cellulose mixture (1:1),
   1.5 parts of sodium dibutyl naphthalene sulphonate,
   19.5 parts of silicic acid
   19.5 parts of Champagne chalk,
   28.1 parts of kaolin;
 c. 25 parts of active substance,
   2.5 parts of isooctylphenoxy-polyoxyethyleneethanol,
   1.7 parts of Champagne chalk/hydroxyethyl cellulose mixture (1:1),
   8.3 parts of sodium aluminium silicate,
   16.5 parts of kieselgur,
   46 parts of kaolin;
 d. 10 parts of active substance,
   3 parts of a mixture of the sodium salts of saturated fatty alcohol sulphates,
   5 parts of naphthalenesulphonic acid/formaldehyde condensate,
   82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates:

The following substances are used to produce (a) a 10%, (b) a 25% and (c) a 50% emulsifiable concentrate:

a. 10 parts of active substance,
 3.4 parts of epoxidised vegetable oil,
 3.4 parts of a combination emulsifier consisting of fatty alcohol polyglycol ether and alkylarylsulphonate calcium salt,
 40 parts of dimethylformamide,
 43.2 parts of xylene;

b. 25 parts of active substance,
 2.5 parts of epoxidised vegetable oil,
 10 parts of alkylarylsulphonate/fatty alcohol-polyglycol ether mixture,
 5 parts of dimethylformamide,
 57.5 parts of xylene;

c. 50 parts of active substance,
 4.2 parts of tributylphenol-polyglycol ether,
 5.8 parts of calcium-dodecylbenzenesulphonate,
 20 parts of cyclohexanone,
 20 parts of xylene.

It is possible to prepare from these concentrates, by dilution with water, emulsions of any desired concentration.

Spray:

The following constituents are used to prepare (a) a 5% spray and (b) a 95% spray:

a. 5 parts of active substance,
 1 part of epichlorohydrin,
 94 parts of ligroin (boiling limits 160°–190° C);

b. 95 parts of active substance,
 5 parts of epichlorohydrin.

EXAMPLE 1

A. Production of α-4-(phenylmercapto-phenoxy)-p-xylene 15.5 g (0.11 mole) of finely pulverised anhydrous potassium carbonate is added to a solution of 22.2 g (0.11 mole) of 4-hydroxydiphenylsulphide in 80 ml of anhydrous acetone, and the mixture is boiled for one hour at reflux temperature. A solution of 18.5 g (0.1 mole) of α-bromo-p-xylene in 30 ml of acetone is added dropwise within 30 minutes and the whole is refluxed for a further 4 hours. In further processing, the reaction solution is filtered off from the solid phase, and the solvent is removed from the filtrate in vacuo. The residue is dissolved in ether, and the solution is washed three times with 10% potassium hydroxide solution and subsequently four times with saturated sodium chloride solution. After drying of the ether phase over sodium sulphate, the solvent is distilled off in vacuo and the residue is recrystallised from hexane/isopropanol.

There is obtained the compound of the formula

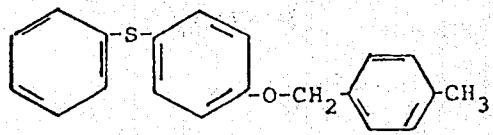

as colourless crystals having a melting point of 97°–97.5° C.

B. Production of the compound of the formula

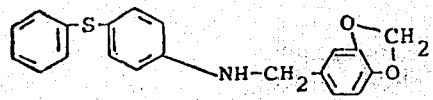

a. A solution of 40.4 g (0.2 mole) of 4-aminodiphenylsulphide in 100 ml of anhydrous benzene is heated to the reflux temperature. To this solution there is added dropwise within 90 minutes a solution of 30 g (0.2 mole) of piperonal in 100 ml of benzene, and the reaction mixture is refluxed for a further 5 hours. After removal of the solvent in a rotary evaporator, the residue is recrystallised from methanol to obtain the compound of the formula

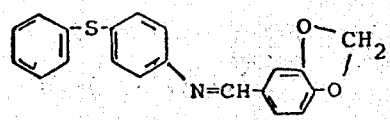

having a melting point of 78°–79° C.

b. 4 g of 5% Pt-C catalyst is added to 41.3 g (0.12 mole) of imine (X) dissolved in 420 ml of dioxane, and in the course of 18½ hours there is then introduced, at room temperature and at a pressure of 760 mm Hg, 2.72 liters of hydrogen. The reaction mixture is filtered and the filtrate is concentrated in a rotary evaporator. The residue is recrystallised from isopropyl ether. There is obtained the compound of the formula

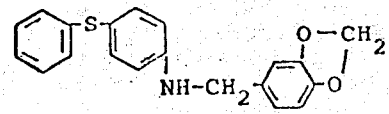

having a melting point of 89°–90° C.

The following compounds are produced in a manner analogous to that previously described:

| Compounds | Physical data |
|---|---|
| 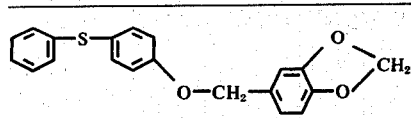 | 82–83° C |
| 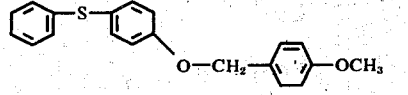 | 93–94° C |

-continued

| Compounds | Physical data |
|---|---|
| C6H5-S-C6H4-O-CH2-C6H4(o-CH3) | 61–62° C |
| C6H5-S-C6H4-O-CH2-C6H4-Cl | 65° C |
| C6H5-S-C6H4-O-CH2-C6H4-O-CH2-C≡CH | 56–57° C |
| C6H5-S-C6H4-S-CH2-C6H4-CH3 | 74–75° C |
| C6H5-S-C6H4-S-CH2-C6H3(O-CH2-O) | 62–63° C |
| C6H5-S-C6H4-S-CH2-C6H4-O-CH2-C≡CH | 86–87° C |
| C6H5-S-C6H4-NH-CH2-C6H4-CH3 | 76–77° C |
| C6H5-S-C6H4-NH-CH2-C6H4-Cl | 85–86° C |
| C6H5-S(O)-C6H4-O-CH2-C6H4-CH3 | 115–117° C |
| C6H5-S-C6H4-O-CH2-C6H4(m-CH3) | 37–40° C |
| C6H5-S-C6H4-O-CH2-C6H4-Br | 68–69° C |
| C6H5-S-C6H4-O-CH2-C6H4(o-Cl) | $n_D^{20}$: 1,6398 |
| C6H5-S-C6H4-O-CH2-C6H4-C2H5 | 53–54° C |
| C6H5-S-C6H4-O-CH2-C6H3(OCH3)2 | 76–78° C |

-continued

| Compounds | Physical data |
|---|---|
| C6H5-S-C6H4-O-CH2-C6H4-C(CH3)3 | 52–53° C |
| C6H5-S-C6H4-O-CH2-C6H4-C3H7(i) |  |
| C6H5-S-C6H4-O-CH2-C6H4(Cl) | 70–71° C |
| C6H5-S-C6H4-S-CH2-C6H4(CH3) | $n_D^{20}$: 1,6616 |
| C6H5-S-C6H4-S-CH2-C6H4(CH3) | $n_D^{20}$: 1,6642 |
| C6H5-S-C6H4-O-CH2-C6H4-C4H9 sec. | $n_D^{20}$: 1,6073 |
| CH3-C6H4-S-C6H4-O-CH2-C6H5 | 72–73° C |
| C6H5-S-C6H4-O-CH2-C6H3(CH3)2 | 59–60° C |
| CH3-C6H4-S-C6H4-O-CH2-C6H4-C(CH3)3 | $n_D^{20}$: 1,6003 |
| C6H5-S-C6H4-O-CH2-C6H3(Cl)2 | 61–63° C |
| C6H5-S-C6H4-O-CH2-C6H4(CH3) | 67–69° C |
| CH3-C6H4-S-C6H4-O-CH2-C6H4-Br | 100–101° C |
| C6H5-S-C6H4-O-CH2-C6H4-J | 69–70° C |
| CH3-C6H4-S-C6H4-O-CH2-C6H4-C2H5 |  |

-continued

| Compounds | Physical data |
|---|---|
| 4-CH₃-C₆H₄-S-C₆H₄-O-CH₂-C₆H₄-4-CH₃ | 100–101° C |
| C₆H₅-S-C₆H₄-O-CH₂-C₆H₄-O-CH₂-CH=CH-Cl | 85–87° C |
| C₆H₅-S-C₆H₄-O-CH₂-C₆H₅ | 69–71° C |
| C₆H₅-S-C₆H₄-O-CH₂-C₆H₄-4-F | 52–54° C |
| C₆H₅-S(O)-C₆H₄-O-CH₂-(3,4-methylenedioxyphenyl) | 114–115° C |
| 4-Cl-C₆H₄-S-C₆H₄-O-CH₂-C₆H₄-4-CH₃ | 105–106° C |
| 4-Cl-C₆H₄-S-C₆H₄-O-CH₂-C₆H₄-4-C₂H₅ | 61–63° C |
| 4-Br-C₆H₄-S-C₆H₄-O-CH₂-C₆H₅ | 103–104° C |
| 4-Br-C₆H₄-S-C₆H₄-O-CH₂-C₆H₄-4-C₂H₅ | 85–87° C |
| C₆H₅-S-C₆H₄-S-CH₂-C₆H₄-O-CH₂-C≡CH | 86–87° C |
| C₆H₅-S-C₆H₄-S-CH₂-C₆H₄-4-Cl | 76–77° C |
| C₆H₅-S-C₆H₄-S-CH(CH₃)-C₆H₄-4-CH₃ | 37–38° C |

-continued

| Compounds | Physical data |
|---|---|
| [structure: phenyl-S(=O)-C6H4-O-CH2-C6H4-Cl] | 97–98° C |
| [structure: phenyl-S(=O)-C6H4-O-CH2-C6H4-ethyl] | $n_D^{20}$: 1,6158 |
| [structure: phenyl-CH2-S-C6H4-O-CH2-C6H4-(CH3)?] | 92–94° C |

EXAMPLE 2

A. Contact action on *Dysdercus-fasciatus* larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the fifth stage of *Dysdercus fasciatus* were placed into the treated dish containing feed and moist cotton wool. The dish was then covered with a perforated lid. After about 10 days, i.e. as soon as the control insects had moulted into adults, the test insects were examined to determine the number of normal adults.

Compounds according to Example 1 exhibited a good action in the above test.

B. Contact action on *Aëdes-aegypti* larvae

About 20 two-day-old larvae of the yellow-fever mosquito (*Aëdes aegypti*) were placed in position in a beaker containing a solution of the active substance (concentration 5 ppm). The beaker was then covered with a perforated lid. After the control insects had moulted into adults, the test insects were examined and the percentage of normal adults in comparison with the control adults was determined.

Compounds according to Example 1 exhibited a good action in the above test.

C. Contact action on *Tenebrio-molitor* pupae

A specific amount of a 0.1% acetonic active-substance solution corresponding to 10 mg of active substance per square meter was transferred by pipet into an aluminium dish and uniformly distributed. After evaporation of the acetone, 10 freshly formed pupae were placed onto the treated surface, and the dish was covered with a perforated lid. After the control insects had left the cocoon as imagines, the test insects were examined to determine the number of normal adults.

Compounds according to Example 1 exhibited a good action in the above test.

EXAMPLE 3

A. Action against *Musca domestica*

An amount in each case of 50 g of CSMA maggot substrate was weighed off in beakers. For each active substance, 2.5 ml of a 1% acetonic solution of the respective substance was transferred by pipet twice to 50 g of maggot substrate each time. After a thorough mixing of the treated substrate, the solvent was allowed to evaporate off. There were then deposited per active substance in each case 25 one-, two- and three-day-old maggots and about 50 fly eggs. After completion of pupation, the pupae were flushed out and counted. After a period of 10 days, the number of emerged flies was counted and hence any effect on metamorphosis was established.

Compounds according to Example 1 exhibited in this test a good action against *Musca domestica*.

B. Action against *Ephestia kühniella*

50 g of wheat flour was made up in two beakers with a specific amount of active substance to give a 5% dust, the concentration being 0.05%. Into each beaker (25 g of flour) there were placed 10 larvae of *Ephestia kühniella*. The pattern of population was ascertained over a period of 8 weeks and the number of moths determined.

Compounds according to Example 1 exhibited a good action in this test against *Ephestia kühniella*.

We claim:
1. A compound of the formula

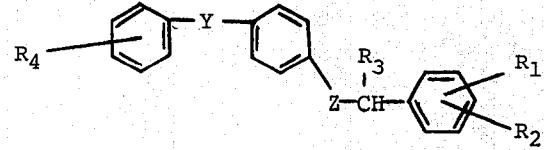

wherein
Y represents —S—,
Z represents —O—,
$R_1$ represents hydrogen, $C_1$–$C_4$-alkyl, or halogen, $R_2$ represents hydrogen, $C_1$–$C_4$-alkyl, or halogen,
$R_3$ represents hydrogen or methyl, and
$R_4$ represents hydrogen, methyl or halogen.

2. A compound according to claim 1 wherein $R_2$, $R_3$ and $R_4$ represent hydrogen.

3. A compound according to claim 2 wherein $R_1$ represents hydrogen, 4-ethyl, 4-i-propyl, 4-methyl, 4-sec.butyl, or 4-bromo.

4. The compound according to claim 3 of the formula

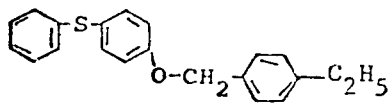

5. The compound according to claim 3 of the formula

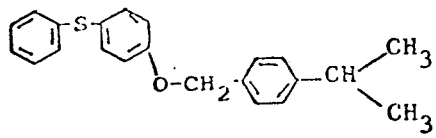

6. The compound according to claim 3 of the formula

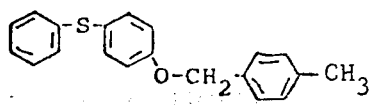

7. The compound according to claim 3 of the formula

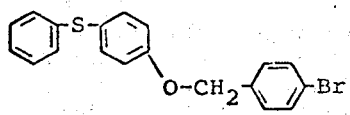

8. The compound according to claim 2 of the formula

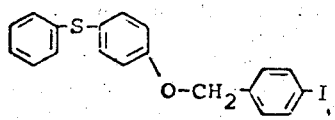

9. The compound according to claim 2 of the formula

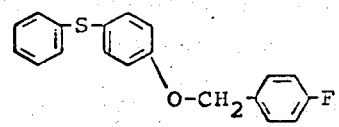

10. The compound according to claim 3 of the formula

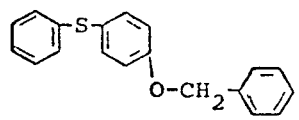

11. The compound according to claim 3 of the formula

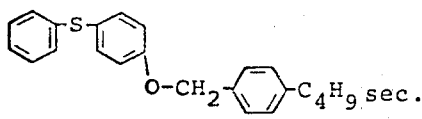

12. An insecticidal composition containing as active component an insecticidally effective amount of a compound according to claim 1, together with a suitable inert carrier therefor.

13. A method for the control of insects which comprises applying to the locus thereof an insecticidally effective amount of a compound according to claim 1.

14. The method of claim 13, wherein in said compound $R_1$, $R_2$ and $R_3$ are hydrogen.

15. The method of claim 14, wherein in said compound $R_1$ represents hydrogen, 4-ethyl, 4-iso-propyl, 4-methyl, 4-sec.butyl or 4-bromo.

16. The method of claim 15, wherein said compound corresponds to the formula

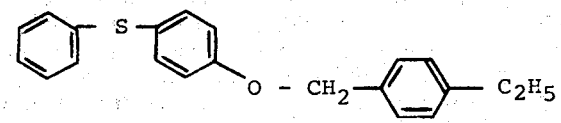

17. The method of claim 15, wherein said compound corresponds to the formula

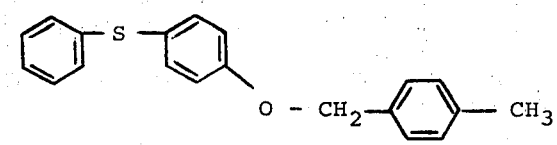

* * * * *